US010955373B2

(12) United States Patent
Wilkinson et al.

(10) Patent No.: US 10,955,373 B2
(45) Date of Patent: Mar. 23, 2021

(54) SYSTEMS, DEVICES, AND METHODS FOR OBJECT QUALITY MONITORING

(71) Applicant: Walmart Apollo, LLC, Bentonville, AR (US)

(72) Inventors: Bruce W. Wilkinson, Rogers, AR (US); David Winkle, Bella Vista, AR (US); Matthew Allen Jones, Bentonville, AR (US); Aaron James Vasgaard, Fayetteville, AR (US); Nicholaus Adam Jones, Fayetteville, AR (US); Robert James Taylor, Rogers, AR (US); Todd Davenport Mattingly, Bentonville, AR (US)

(73) Assignee: Walmart Apollo, LLC, Bentonville, AR (US)

( * ) Notice: Subject to any disclaimer, the term of this patent is extended or adjusted under 35 U.S.C. 154(b) by 314 days.

(21) Appl. No.: 15/782,074

(22) Filed: Oct. 12, 2017

(65) Prior Publication Data
US 2018/0106742 A1    Apr. 19, 2018

Related U.S. Application Data

(60) Provisional application No. 62/408,660, filed on Oct. 14, 2016.

(51) Int. Cl.
*G01N 27/04* (2006.01)
*G01D 21/02* (2006.01)
(Continued)

(52) U.S. Cl.
CPC ........... *G01N 27/048* (2013.01); *G01D 11/00* (2013.01); *G01D 21/02* (2013.01); *G01M 3/00* (2013.01); *G01N 33/025* (2013.01)

(58) Field of Classification Search
None
See application file for complete search history.

(56) References Cited

U.S. PATENT DOCUMENTS 5,067,356 A  *  11/1991  Businger .................. G01P 5/245
                                                 73/863.02
5,159,959 A  *  11/1992  Bohm ....................... B65B 1/46
                                                 141/1
(Continued)

FOREIGN PATENT DOCUMENTS

WO    WO-9803868 A1  *  1/1998  ......... G01N 33/0006
WO    2006116665 A1    11/2006

OTHER PUBLICATIONS

Savi, Best Practices in Improving Container Management and Increasing Supply Chain Efficiencies: A Five Step Plan to Implement Container Management Solutions and Improve Supply Chain Visibility, Dec. 23, 2013.
(Continued)

*Primary Examiner* — Fekadeselassie Girma
(74) *Attorney, Agent, or Firm* — Fitch, Even, Tabin & Flannery, LLP

(57) ABSTRACT

A technique for monitoring the quality of objects is disclosed. A container includes a multiple sensors and is configured to receive an object. The sensors monitor various metrics associated with the quality of the object, and a display is affixed to the container for displaying a visual indication of the quality of the object. The visual indication is based on data collected from the sensors. A quality monitoring module is executed by a processor to control the sensors to switch operation between a first mode of operation and a second mode of operation based on a detected change in one of the metrics monitored by the sensors.

23 Claims, 6 Drawing Sheets

(51) Int. Cl.
*G01D 11/00* (2006.01)
*G01M 3/00* (2006.01)
*G01N 33/02* (2006.01)

(56) References Cited

U.S. PATENT DOCUMENTS

| | | | | |
|---|---|---|---|---|
| 5,581,367 | A * | 12/1996 | Oogiri | H04N 1/00912 |
| | | | | 358/404 |
| 7,196,622 | B2 | 3/2007 | Lambright et al. | |
| 8,218,514 | B2 | 7/2012 | Twitchell, Jr. | |
| 8,615,374 | B1 * | 12/2013 | Discenzo | G01D 21/02 |
| | | | | 702/127 |
| 8,694,260 | B1 * | 4/2014 | Jimeno | G06Q 10/00 |
| | | | | 702/14 |
| 9,098,825 | B2 | 8/2015 | Bashkin | |
| 10,145,617 | B1 * | 12/2018 | Young | F27D 21/0014 |
| 2006/0012480 | A1 * | 1/2006 | Klowak | G06K 7/0008 |
| | | | | 340/572.1 |
| 2006/0213904 | A1 * | 9/2006 | Kates | B65D 79/02 |
| | | | | 219/702 |
| 2007/0050271 | A1 | 3/2007 | Ufford et al. | |
| 2007/0241756 | A1 * | 10/2007 | Mizukami | G01N 27/048 |
| | | | | 324/444 |
| 2008/0183599 | A1 | 7/2008 | Hill et al. | |
| 2011/0245680 | A1 * | 10/2011 | Hunt | A61B 8/00 |
| | | | | 600/459 |
| 2014/0051115 | A1 * | 2/2014 | Hakalehto | C12Q 1/04 |
| | | | | 435/34 |
| 2014/0166694 | A1 * | 6/2014 | Otto | B67D 1/0888 |
| | | | | 222/95 |
| 2015/0128733 | A1 * | 5/2015 | Taylor | H02J 50/001 |
| | | | | 73/865.8 |
| 2015/0272473 | A1 * | 10/2015 | Zafiroglu | G16H 40/63 |
| | | | | 600/302 |
| 2015/0371522 | A1 * | 12/2015 | Mravyan | A61G 7/05776 |
| | | | | 340/573.1 |
| 2016/0169826 | A1 * | 6/2016 | Youssi | G01N 33/46 |
| | | | | 324/664 |
| 2016/0296421 | A1 * | 10/2016 | Atkins, Jr. | A61M 35/006 |
| 2017/0030861 | A1 * | 2/2017 | Jiao | G01N 27/223 |
| 2017/0284840 | A1 * | 10/2017 | Mino | G01D 21/02 |
| 2018/0108242 | A1 * | 4/2018 | Wilkinson | G08B 31/00 |
| 2018/0168391 | A1 * | 6/2018 | Eriksson | A47J 31/545 |
| 2018/0188182 | A1 * | 7/2018 | Jones | G01N 33/04 |
| 2019/0185237 | A1 * | 6/2019 | Greenberg | B65D 73/00 |

OTHER PUBLICATIONS

National Aeronautics and Space Administration, Smart Enclosure using RFID for Inventory Tracking, http://lltechnology.nasa.gov/, May 2015.

* cited by examiner

SYSTEMS, DEVICES, AND METHODS FOR OBJECT QUALITY MONITORING

CROSS-REFERENCE TO RELATED PATENT APPLICATIONS

This application claims priority to U.S. Provisional Application No. 62/408,660 filed on Oct. 14, 2016, the content of which is hereby incorporated by reference in its entirety

BACKGROUND

Various types of containers can be used to store or transport objects from one location to another. Such objects can include perishable items, such as, for example, produce or other consumable products.

SUMMARY

Embodiments of the present invention utilize multiple sensors to monitor the quality of objects within a container. In some embodiments, a display renders a visual indication of the quality of the objects based on the sensor data. The sensors are switched between a first mode of operation and a second mode of operation based on detected changes in sensor data.

In one embodiment, a quality monitoring system is disclosed. The system includes a container configured to receive an object, multiple sensors configured to monitor various metrics associated with a quality of the object within the container, and a display configured to display a visual indication of the quality of the object within the container. The display is affixed to the container. The visual indication of the quality of the object is based, at least in part, on data collected from the sensors. The system also includes a quality monitoring module executed by a processor in a processing device. The quality monitoring module is in communication with the sensors and the display and is configured to control the sensors to switch operation between a first mode of operation and a second mode of operation based on a detected change in one of the metrics associated with a quality of an object being monitored by the sensors. In another embodiment, a method for monitoring the quality of objects includes monitoring metrics associated with a quality of an object within a container using multiple sensors. The method also includes displaying, via a display affixed to the container, a visual indication of the quality of the object within the container. The visual indication of the quality of the object is based, at least in part, on data collected from the sensors. The method also includes controlling the sensors to operate in a first mode of operation, and controlling the sensors to operate in a second mode of operation. The method also includes instructing the sensors to switch between the first mode of operation and second mode of operation based on a detected change in one of the metrics associated with a quality of an object within the container.

Additional combinations and/or permutations of the above examples are envisioned as being within the scope of the present disclosure. It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein.

BRIEF DESCRIPTION OF THE DRAWINGS

The skilled artisan will understand that the drawings primarily are for illustrative purposes and are not intended to limit the scope of the inventive subject matter described herein. The drawings are not necessarily to scale; in some instances, various aspects of the inventive subject matter disclosed herein may be shown exaggerated or enlarged in the drawings to facilitate an understanding of different features. In the drawings, like reference characters generally refer to like features (e.g., functionally similar and/or structurally similar elements).

The foregoing and other features and advantages provided by the present disclosure will be more fully understood from the following description of exemplary embodiments of the present invention when read together with the accompanying drawings, in which.

DETAILED DESCRIPTION

Figure 1:
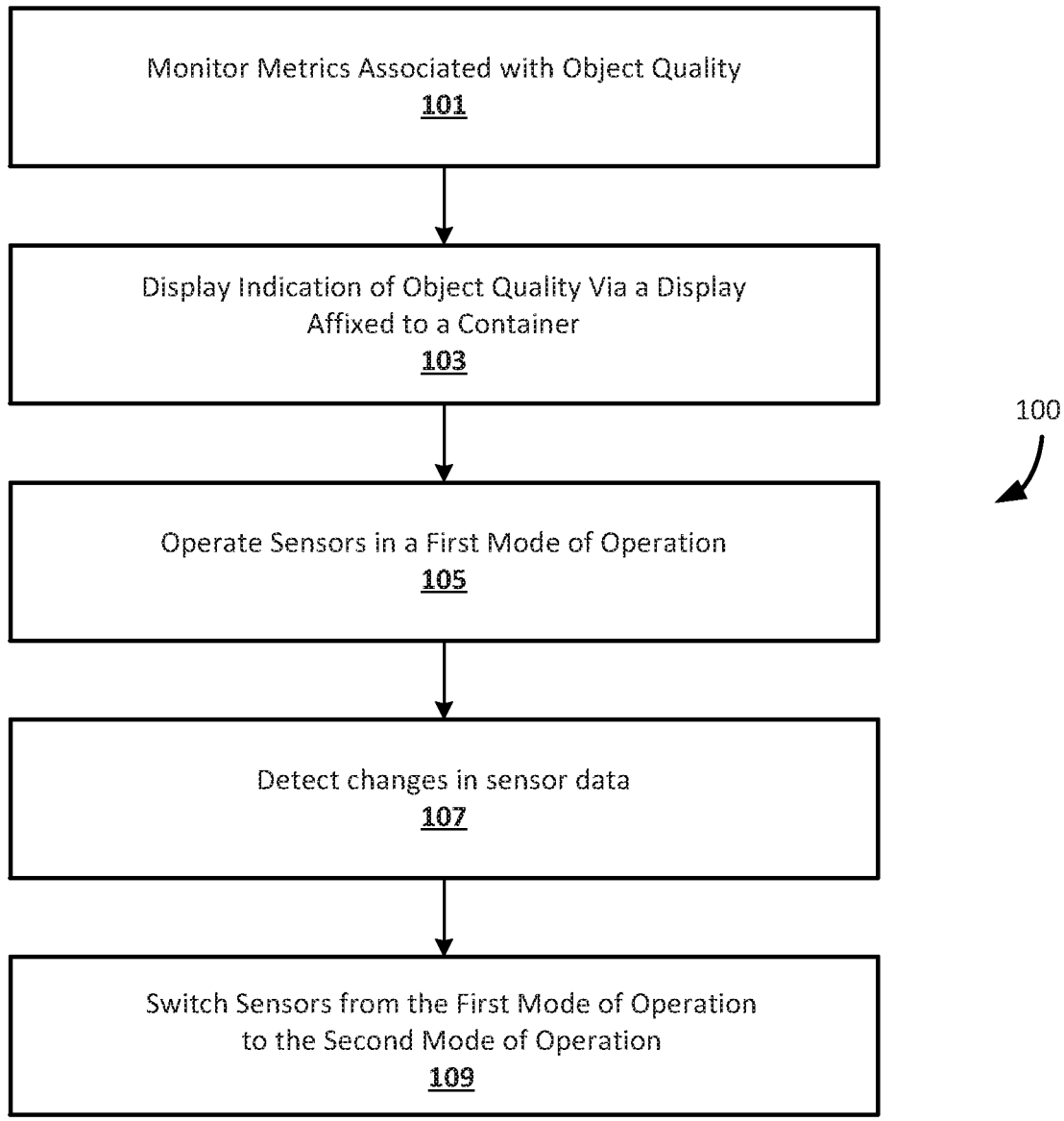
FIG. 1 is a flowchart illustrating an exemplary method for monitoring the quality of objects, according to an embodiment.

Following below are more detailed descriptions of various concepts related to, and embodiments of, inventive methods, devices, and systems for monitoring the quality of objects. It should be appreciated that various concepts introduced above and discussed in greater detail below may be implemented in any of numerous ways, as the disclosed concepts are not limited to any particular manner of implementation. Examples of specific implementations and applications are provided primarily for illustrative purposes.

As used herein, the term "includes" means "includes but is not limited to", the term "including" means "including but not limited to". The term "based on" means "based at least in part on".

In accordance with some embodiments, methodologies, systems, devices, and non-transitory computer-readable media are described herein to facilitate monitoring the quality of objects within a container. In exemplary embodiments, the container includes various sensors, such as pressure sensors, temperature sensors, off-gas sensors, weight sensors, moisture sensors, or other sensors that can monitor various metrics associated with the quality of the object or objects in the container. For example, a temperature sensor can monitor whether there is an undesirable increase in temperature within the container, a moisture sensor can detect whether there is a spill within the container, and an off-gas sensor can detect whether produce within the container is damaged or spoiled. In some embodiments, the container can be a sealable container that creates an air-tight seal around the objects in the container. Alternatively, the sensors could be located on the outside of the container and configured to monitor environmental metrics that would influence the interior of the container. Embodiments may use spectrometers for chemical compound detection. In one embodiment, the spectrometers may be used for off-gas detection and/or detection of volatile chemicals (spills) or to monitor the environment the product is kept in (e.g.: high oxygen, ethylene (ripening chamber), nitrogen or other inert gases, etc.).

In some embodiments, the sensors can operate in various modes of operation in which different subsets of sensors are active or different sensitivity thresholds or other operating characteristics are applied to the sensors. For example, a change in mode may refer to a change in the frequency with which sensors sample data, may refer to a change in the types of operations conducted by already active sensors, may refer to the activation of new types of sensors and/or the de-activation of currently active sensors or some combination of these. A quality monitoring module can be executed by a processor of a computing system in order to control the sensors to operate in a first mode of operation or a second mode of operation. The quality monitoring module can also control the sensors to switch between the first mode of operation and the second mode of operation. In some embodiments, the quality monitoring module can instruct the sensors to switch modes of operation based on a detected change in one of the various metrics monitored by the sensors. For example, a sensor may detect an increased amount of heat in a container which may lead to a switch to a mode whereby the temperature is checked more frequently. Alternatively, the detection of an off-gas in a container may possibly foreshadow a problem and so lead to the activation of a moisture sensor in the container to obtain moisture readings in the container. In other embodiments, the sensors can switch modes of operation based on a change in the location of the container. In some embodiments, a first subset of the sensors is active during the first mode of operation, and a second subset of the sensors is active during the second mode of operation. In another embodiment, the same subset of sensors is active but operates in a different manner in the second mode of operation such as by altering a frequency of sampling or taking additional types of measurements. In one embodiment, the container is configured to be moved from one location to a second location, and the sensors can dynamically transition from a first mode of operation to a second mode of operation between the origin and destination.

In one example embodiment, the container includes a display configured to show an indication of the quality of the object in the container based on sensor data. The display can be a screen or digital display that can render, for example, a barcode, a color-coded indicator, or text. The display can also render an indication of the current mode of operation of the container. The display can be updated to reflect changes in the quality of the object in the container or changes in the mode of operation of the sensors.

In some embodiments, the container can include a speaker or other audio device that can assist in locating the container. The audio device can also be used, in some embodiments, to indicate the quality of objects within the container or to indicate the current mode of operation of the container.

Exemplary embodiments are described below with reference to the drawings. One of ordinary skill in the art will recognize that exemplary embodiments are not limited to the illustrative embodiments, and that components of exemplary systems, devices and methods are not limited to the illustrative embodiments described below.

FIG. 1 is a flowchart illustrating a method 100 for monitoring the quality of objects, in accordance with an exemplary embodiment. It will be appreciated that the method is programmatically performed by one or more computer-executable processes executing on, or in communication with, one or more computing systems or processors described further below. In step 101, multiple sensors are used to monitor various metrics associated with a quality of an object within a container. In some embodiments the sensors can be attached to the container, while in other embodiments they are integral to the container itself. The container may be a sealable container that, in some embodiments, can create a substantially air-tight seal when a lid of the container is closed. The sensors can include, for example, pressure sensors, temperature sensors, off-gas sensors, weight sensors, moisture sensors, or any other sensor configured to monitor metrics relating to the quality of the object within the container. The sensors may also include an infrared or optical reader configured to read a barcode or other machine-readable code associated with the object. In other embodiments, the sensors may include an RFID reader configured to read an RFID tag associated with the object. In some embodiments, the types of sensors used, as well as sensitivity thresholds associated with those sensors, can depend on the types of objects the container is configured to hold. For example, an off-gassing sensor may be tuned differently when implemented with a container configured to hold apples than with a container configured to hold tomatoes because of different expected amount of off-gassing. In some embodiments, one or more of the sensors can be configured to monitor the amount of time the object has been within the container.

In step 103, a display affixed to the container displays a visual indication of the quality of the object within the container. The visual indication of the quality of the object is based, at least in part, on data collected from the sensors. The display can include, for example, an e-paper display, a light-emitting diode (LED) display, an organic LED (OLED) display, a liquid-crystal display (LCD), or any other display suitable for presenting a visual indication of the quality of the object. In some embodiments, the visual indication can include a human-readable indication, such as a textual message or a color-coded indication. Additionally or alternatively, the visual indication can include a machine-readable code, such as a barcode, that can be scanned and read by an electronic device. In one embodiment, the display is in direct communication with the sensors and updates the visual indication as sensor data changes. In another embodiment, the display receives the sensor data indirectly via a monitoring module being executed on a computing device that is in communication with the sensors.

In step 105, a quality monitoring module is executed by a processor to control the sensors to operate in a first mode of operation. The quality control module is in communication with the sensors and the display. When operating in the first mode of operation, certain sensors in the container are active and operate in a defined manner.

In step 107, the quality monitoring module may detect a change in the sensor data. The detected change may be a change in one of the various metrics, monitored in step 101, associated with the quality of the object in the container. For example, an elevation in the temperature or moisture level in the container may be detected by at least one of the containers in the sensor.

In step 109, the quality monitoring module controls the sensors to switch between the first mode of operation and a second mode of operation. In the second mode of operation, the same or different sensors in the container may be active and/or the types of operations conducted by the sensors may differ from those conducted in the first mode. As a non-limiting example, a sensor may sample data more or less often and may alter the duration of the sampling. Alternatively, at least some of the sensors that are active in the second mode may be different from the sensors that are active in the first mode. In one example embodiment, the container includes a number of produce items, and in the first mode of operation a weight sensor is configured to monitor the weight of the produce. In this example, once a predetermined amount of time has passed, the quality monitoring module controls the sensors to switch to the second mode of operation, in which a gas sensor is configured to monitor the off-gassing of the produce within the container. In exemplary embodiments, the off-gas sensor can include a spectrometer.

Figure 2:
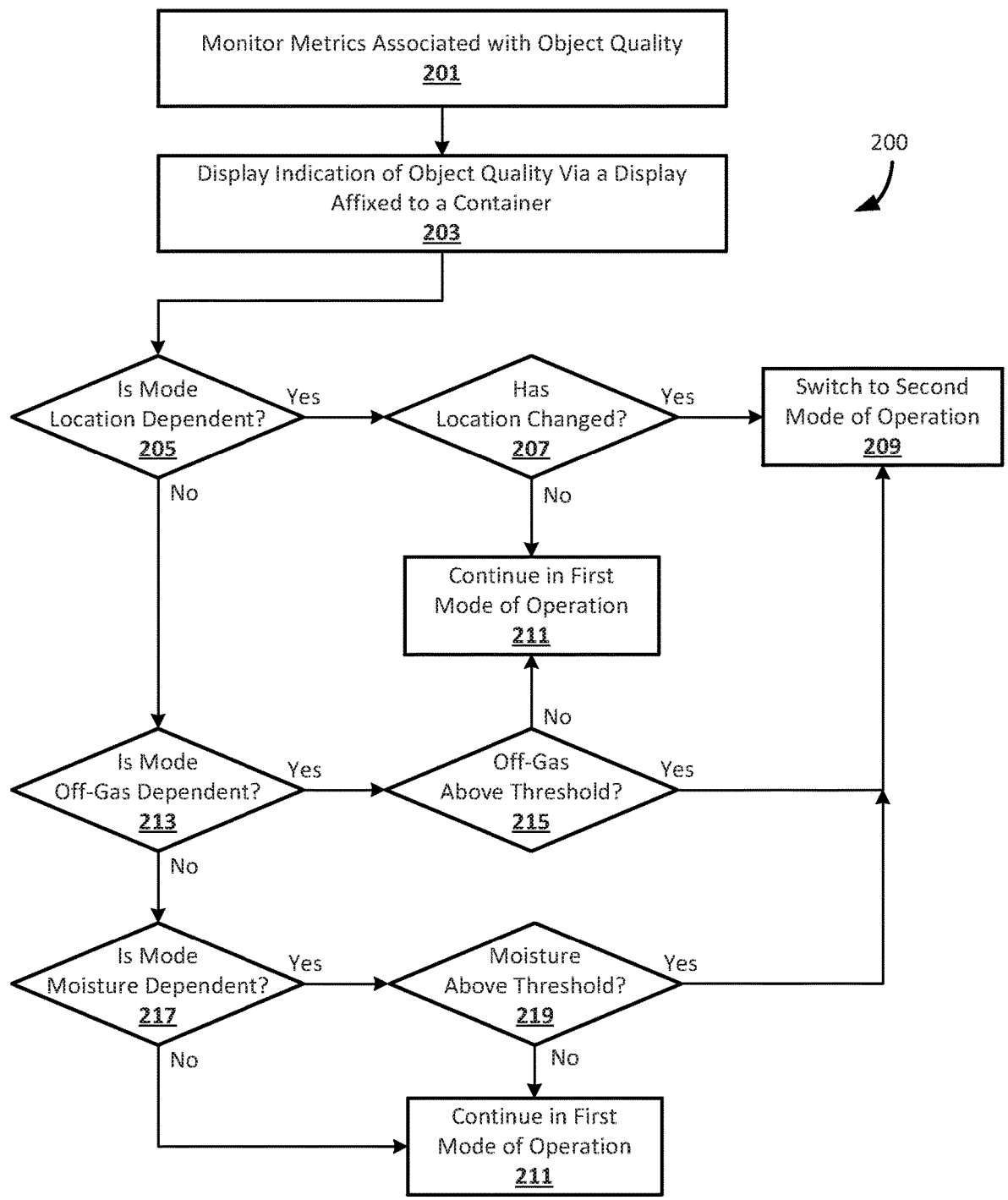
FIG. 2 is a flowchart illustrating another exemplary method for monitoring the quality of objects based on different types of quality criteria, according to an embodiment.

FIG. 2 is a flowchart illustrating another method 200 for monitoring the quality of objects, in accordance with an exemplary embodiment. It will be appreciated that the method is programmatically performed by one or more computer-executable processes executing on, or in communication with, one or more computing systems or processors described further below. In step 201, multiple sensors are used to monitor various metrics associated with a quality of an object within a container. The container may be a sealable container, in some embodiments, that can create a substantially air-tight seal when a lid of the container is closed such that the sensors can monitor various metrics within the container in a substantially sealed environment. The sensors can include, for example, pressure sensors, temperature sensors, off-gas sensors, weight sensors, moisture sensors, or any other sensor configured to monitor metrics relating to the quality of the object within the container. The sensors may also include an infrared or optical reader configured to read a barcode or other machine-readable code associated with the object. The sensors may also include an optical sensor or camera configured to monitor the color of the object. For example, an optical sensor can monitor the color of certain types of produce in order to detect spoilage. Furthermore, the sensors may include one or more microphones configured to capture sounds within the container, such as objects jostling around or glass breaking. The sounds of the objects can be used, in some embodiments, to determine the ripeness of the objects, to determine if the objects are damaged, or to determine if one or more objects in the container are broken. In some embodiments, one or more of the sensors can be configured to monitor the geographical location of the container. In some embodiments, the container can be Wi-Fi enabled or can include inertial sensors, one or more RFID tags, a global positioning system tracking unit, barometric pressure sensors, near-field communication sensors, or other location tracking technologies. Initially, a quality monitoring module executed by a processor is in communication with the sensors and configured to control the sensors such that the sensors operate in a first mode of operation.

In step 203, a display affixed to the container displays a visual indication of the quality of the object within the container. The display can include, for example, an e-paper display, a LED display, an OLED display, a LCD, or any other display suitable for presenting a visual indication of the quality of the object. The visual indication of the quality of the object is based, at least in part, on data collected from the sensors. For example, if a weight sensor in the container determines that the object is lighter than expected, the display can show a notification indicating that the weight of the object is inconsistent with the expected weight of that object. In another example, if an off-gas sensor determines that produce in the container is emitting too much off-gas, such as ethylene, the display can show a notification indicating that the produce is damaged or over-ripe. In some embodiments, the visual indication can include a human-readable indication, such as a textual message or a color-coded indication. Additionally or alternatively, the visual indication can include a machine-readable code, such as a barcode, that can be scanned and read by an electronic device.

In step 205, the system determines whether the mode of operation of the sensors is dependent on the geographical location of the container. If the mode of operation of the sensors is dependent on the location of the container, the method continues to step 207 where the quality monitoring module determines whether the location of the container has changed sufficiently in order to switch modes of operation of the sensors. In one example embodiment, the container can be configured to hold produce while it is transported from a first location to a second location, and the quality monitoring module may be configured to control the sensors to switch from a first mode of operation to a second mode of operation when the container moves from the a storage location to a shipping vessel. In some embodiments, different quality metrics are of more importance when an object is in storage than when the object is being shipped from one location to another. For example, pressure sensors can monitor whether produce within the container is being shaken too much during transit, while an off-gas sensor can monitor whether the produce is damaged or spoiled during storage, and a weight sensor can monitor the quantity of the produce in the container when the container is in a display area.

If the container has changed location, the quality monitoring module controls the sensors to switch to the second mode of operation in step 209. In some embodiments, a different subset of sensors is active during the second mode of operation than during the first mode of operation. In other embodiments, a different sensitivity threshold or other change in operating characteristics is applied to the active sensors during the second mode of operation than during the first mode of operation. If it is determined in step 207 that the container has not changed location sufficiently, the sensors continue to operate in the first mode of operation in step 211.

If it is determined in step 205 that the mode of operation of the sensors is not dependent on the geographical location of the container, the method continues to step 213 where the system determines whether the mode of operation of the sensors is dependent on off-gas levels within the container. If the mode of operation of the sensors is dependent on the off-gas levels within the container, the method continues to step 215 where the quality monitoring module determines whether the off-gas level within the container has increased above a threshold value. In one example embodiment, the container can be configured to hold produce while it is transported from a first location to a second location, and the quality monitoring module may be configured to adjust the sensitivity of the sensors in a second mode of operation if the off-gas levels within the container are above a specific threshold value. If the off-gas level is above the threshold value, the quality monitoring module controls the sensors to switch to a second mode of operation in step 209. In some embodiments, a different subset of sensors is active during the second mode of operation than during the first mode of operation. In other embodiments, a different sensitivity threshold or other change in operating characteristics is applied to the active sensors during the second mode of operation than during the first mode of operation. If it is determined in step 215 that the off-gas level within the container is not above the threshold value, the sensors continue to operate in the first mode of operation in step 211.

If it is determined in step 213 that the mode of operation of the sensors is not dependent on the off-gas levels in the container, the method continues to step 217 where the system determines whether the mode of operation of the sensors is dependent on moisture levels within the container. If the mode of operation of the sensors is dependent on the moisture levels within the container, the method continues to step 219 where the quality monitoring module determines whether the moisture level within the container has increased above a threshold value. In one example embodiment, the container can be configured to hold containers of liquids, and detecting moisture levels above the threshold value can indicate a leak in one of the containers of liquid. If the moisture level in the container is above the threshold value, the quality monitoring module controls the sensors to switch to a second mode of operation in step 209. In some embodiments, a different subset of sensors is active during the second mode of operation than during the first mode of operation. In other embodiments, a different sensitivity threshold or other change in operating characteristics is applied to the active sensors during the second mode of operation than during the first mode of operation. If it is determined in step 219 that the moisture level within the container is not above the threshold value, the sensors continue to operate in the first mode of operation in step 211.

Figure 3:
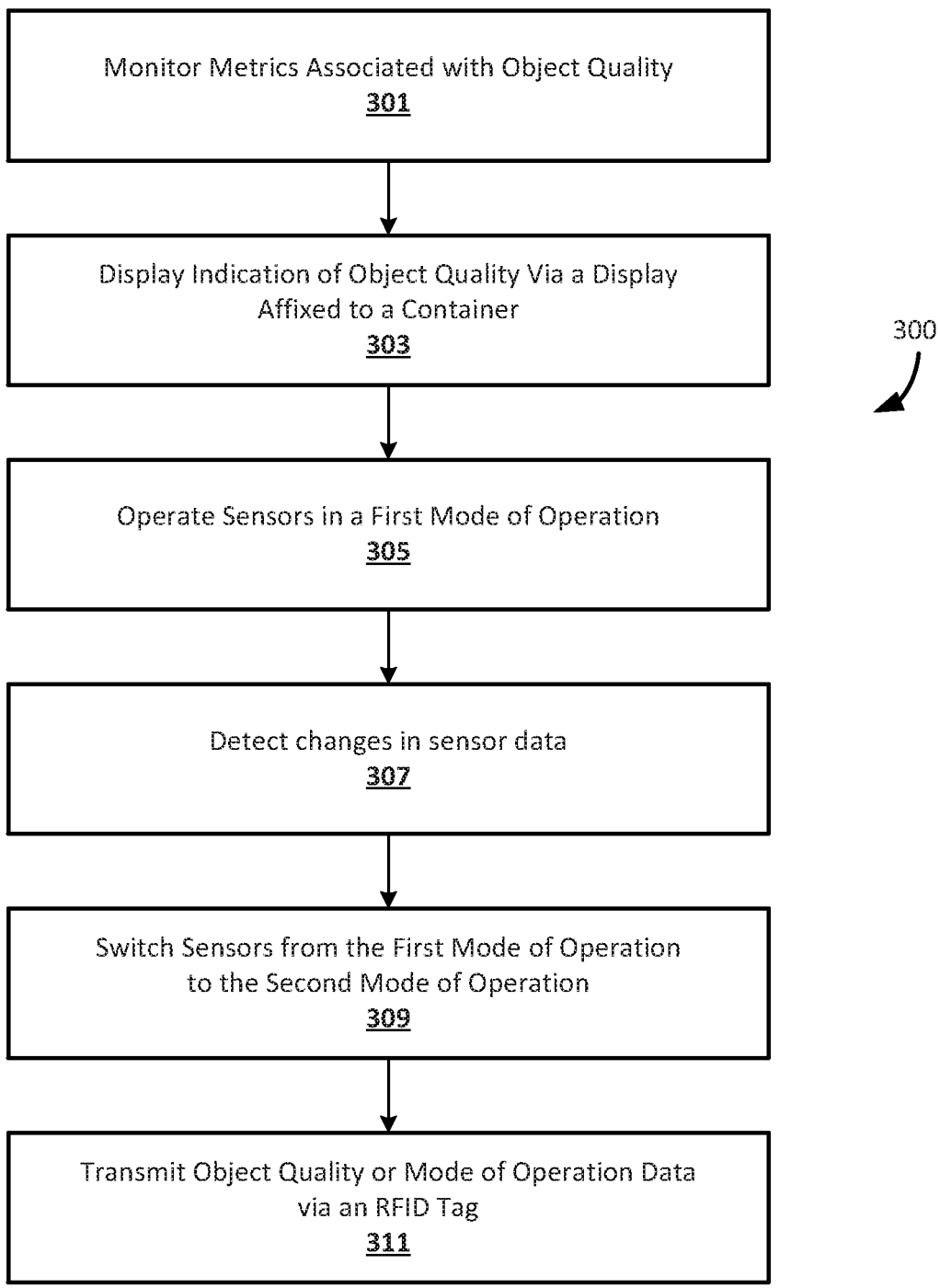
FIG. 3 is a flowchart illustrating another exemplary method for monitoring the quality of objects and transmitting data via an RFID tag, according to an embodiment.

FIG. 3 is a flowchart illustrating another method 300 for monitoring the quality of objects, in accordance with an exemplary embodiment. It will be appreciated that the method is programmatically performed by one or more computer-executable processes executing on, or in communication with, one or more computing systems or processors described further below. In step 301, multiple sensors in a container are used to monitor various metrics associated with the quality of an object within the container. In some embodiments, the container can include a lid that can create a substantially air-tight seal within the container when closed. The sensors can include, for example, pressure sensors, temperature sensors, off-gas sensors, weight sensors, moisture sensors, or any other sensor configured to monitor metrics relating to the quality of the object within the container. In some embodiments, the types of sensors in the container, as well as the sensitivity thresholds associated with those sensors, can depend on the types of objects the container is configured to hold. For example, if the container is configured to hold containers of liquid or a potentially hazardous chemical, the container can be configured with moisture sensors or with sensors that can detect the presence of toxic fumes or vapors.

In step 303, a display affixed to the container displays a visual indication of the quality of the object within the container. The visual indication of the quality of the object is based, at least in part, on data collected from the container's sensors. The display can include, for example, an e-paper display, a LED display, an OLED display, a LCD, or any other display suitable for presenting a visual indication of the quality of the object. In some embodiments, the visual indication can be a color-coded indication. In one embodiment, if a moisture sensor detects that there is a spill within the container, the display can show a color-coded message indicating that there is a spill in the container.

In step 305, a quality monitoring module is executed by a processor to control the sensors in the container to operate in a first mode of operation. The quality control module is in communication with the sensors and with the display and can control whether each individual sensor is active. The quality monitoring module can also control the sensitivity of the sensors, in some embodiments. In some embodiments, when operating in the first mode of operation, a first subset of the sensors is active and is operating at a first sensitivity threshold value.

In step 307, the quality monitoring module detects a change in the sensor data that is being monitored. The detected change may be a change in one of the various metrics, monitored in step 301, associated with the quality of the object in the container.

In step 309, the quality monitoring module controls the sensors to switch between the first mode of operation and a second mode of operation. For example, the sensors can switch from a first mode of operation, in which only weight and temperature are measured, to a second mode of operation in which off-gassing is measured, in response to the temperature within the container rising to a particular level. When operating in the second mode of operation, a second subset of the sensors may be active. In one example embodiment, the container includes a number of produce items, and in a first mode of operation a temperature sensor is configured to monitor the temperature within the container. In this example, if the temperature within the container increases beyond a predetermined threshold value, the quality monitoring module controls the sensors to switch to the second mode of operation, in which a gas sensor is configured to monitor the off-gassing of the produce within the container. In some embodiments, the quality monitoring module can control the sensors to switch back to the first mode of operation, or to switch to a third mode of operation in which a third subset of sensors is active in response to a change in one of the quality metrics associated with the object in the container, or in response to a change in the location of the container. It will be appreciated that various modes of operation, in which different subsets of sensors are active and operating at different sensitivity levels, are possible and the present invention is not intended to be limited to any particular mode or modes of operation, unless stated otherwise.

In step 311, an RFID tag associated with the container transmits data to the quality monitoring module representative of the quality of the object in the container or the current mode of operation of the sensors. In some embodiments, the container can include an RFID tag that can transmit data to an RFID reader representative of the quality of object in the container or the mode of operation of the sensors. This RFID tag can be updated if the quality of the object changes or if the mode of operation of the sensors changes.

Figure 4:
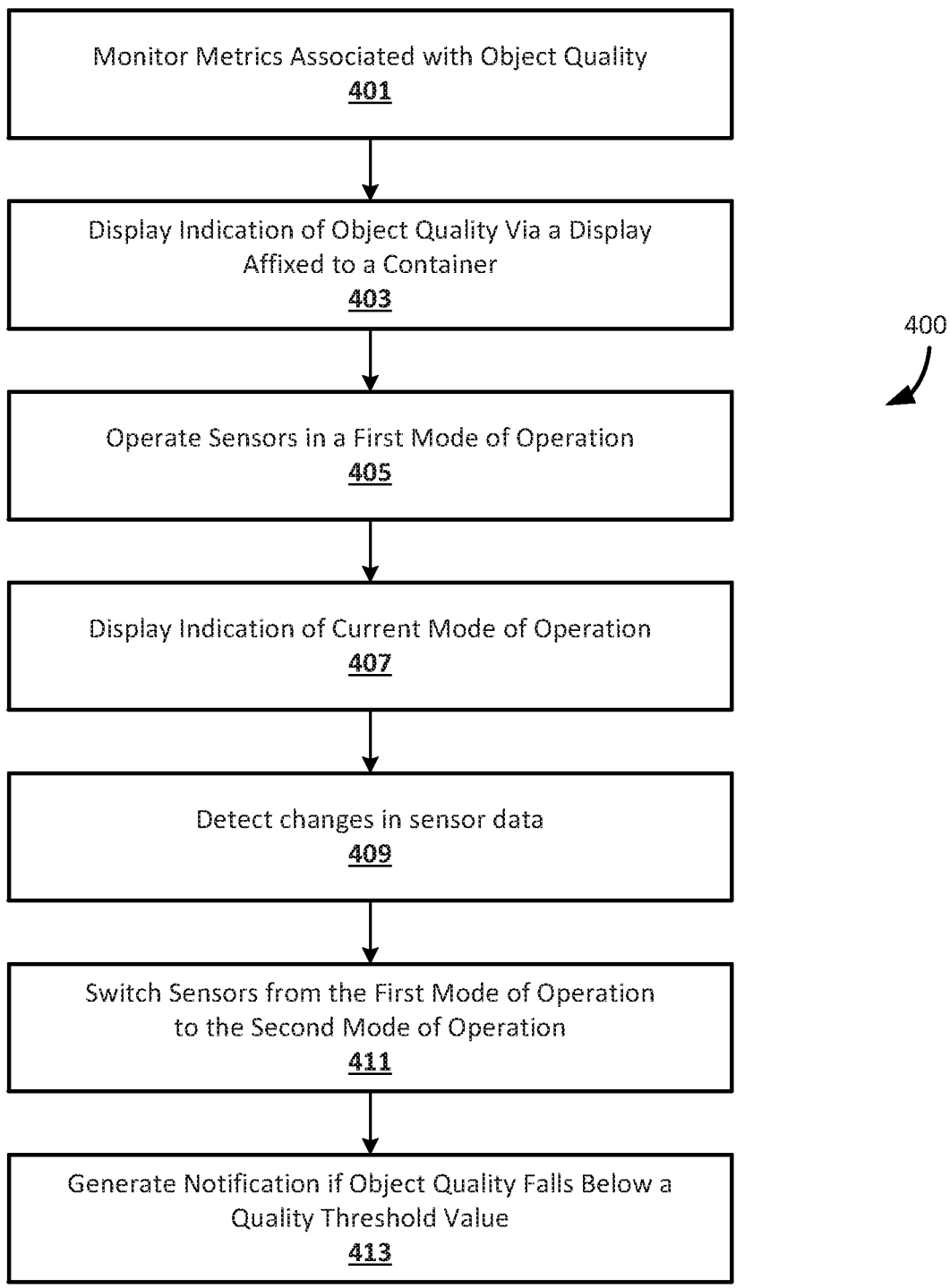
FIG. 4 is a flowchart illustrating another exemplary method for monitoring the quality of objects and generating notifications, according to an embodiment.

FIG. 4 is a flowchart illustrating another method 400 for monitoring the quality of objects and generating a notification based thereon, in accordance with an exemplary embodiment. It will be appreciated that the method is programmatically performed by one or more computer-executable processes executing on, or in communication with, one or more computing systems or processors described further below. In step 401, multiple sensors in a container are used to monitor various metrics associated with the quality of an object within the container. The sensors can include, for example, pressure sensors, temperature sensors, off-gas sensors, weight sensors, moisture sensors, or any other sensor configured to monitor metrics relating to the quality of the object within the container. In some embodiments, the types of sensors in the container, as well as the sensitivity thresholds associated with those sensors, can depend on the amount of time an object has been disposed within the container. For example, if the container is configured to hold perishable items, such as produce, different sensors may be active depending on how long the produce has been within the container.

In step 403, a display affixed to the container displays a visual indication of the quality of the object within the container. The visual indication is based, at least in part, on data collected from the container's sensors. The display can include, for example, an e-paper display, a LED display, an OLED display, a LCD, or any other display suitable for presenting a visual indication of the quality of the object. In some embodiments, the visual indication can be an easily understood text message. For example, if produce within the container is currently fresh and all readings from the sensors indicate that the quality of the produce is satisfactory, the display can show the word "Fresh" or some other suitable message.

In step 405, a quality monitoring module is executed by a processor to control the sensors in the container to operate in a first mode of operation. The quality control module is in communication with the sensors and can control whether each individual sensor is active, as well as the sensitivity of each sensor. As discussed above, the sensors can operate in various modes of operation depending on the location of the container, a change in one of the metrics associated with the quality of the object in the container, or the amount of time the object has been disposed within the container.

In step 407, the display renders a visual indication of the current mode of operation of the sensors. In some embodiments, the visual indication of the mode of operation can be displayed adjacent to the visual indication of the quality of the object, which is displayed in step 403.

In step 409, the quality monitoring module detects a change in the sensor data that is being monitored. The detected change may be a change in one of the various metrics, monitored in step 301, associated with the quality of the object in the container.

In step 411, the quality monitoring module controls the sensors to switch between the first mode of operation and a second mode of operation. In some embodiments, the quality monitoring module can instruct the sensors to switch modes of operation based on a detected change in one of the various metrics, monitored in step 401, associated with the quality of the object in the container. In some embodiments, the visual indication of the current mode of operation of the sensors, displayed in step 407, can be updated to reflect the new mode of operation.

In step 413, the quality monitoring module generates a notification if the quality of the object in the container falls below a quality threshold value based on detected sensor data. For example, if an off-gas sensor detects too much ethylene from produce within the container, a notification can be generated and transmitted to an individual responsible for the produce so that the produce can be inspected.

Figure 5:
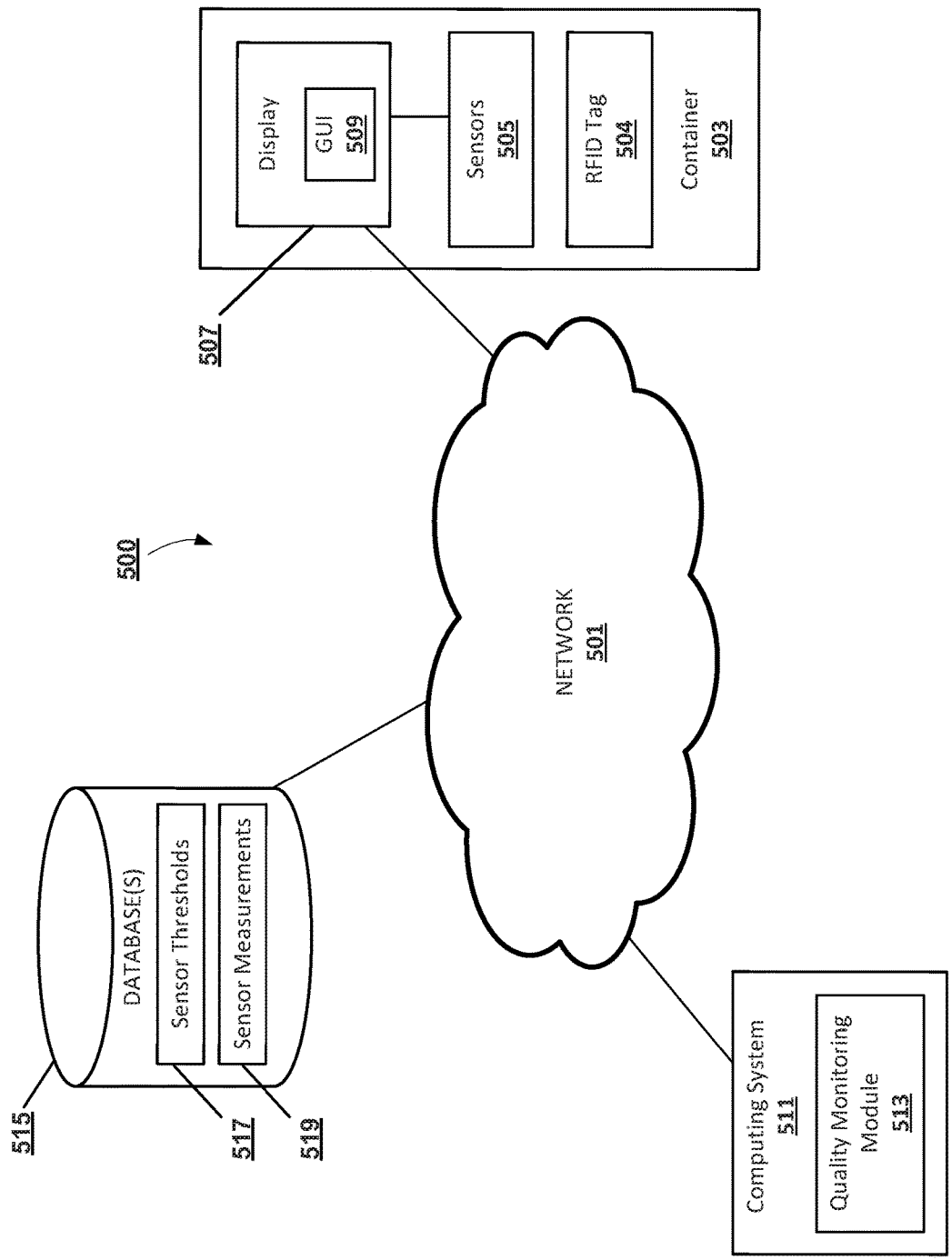
FIG. 5 is a diagram of an exemplary network environment suitable for a distributed implementation of an exemplary embodiment.

FIG. 5 illustrates a network diagram depicting a system 500 suitable for a distributed implementation of exemplary embodiments. The system 500 can include a network 501, a container 503 having sensors 505 and an RFID tag 504, a display 507, a computing system 511, and a database 515. As will be appreciated, various distributed or centralized configurations may be implemented. In exemplary embodiments, computing system 511 can store a quality monitoring module 513 which can implement one or more of the processes described herein with reference to FIGS. 1-4, or portions thereof. It will be appreciated that the module functionality may be implemented as a greater number of modules than illustrated, and that the same computing system or server could host one or more modules. The database 515 can store the sensor thresholds 517 and the sensor measurements 519 associated with objects in the container 503, in exemplary embodiments.

In exemplary embodiments, the display 507 can display a GUI 509. In some embodiments, the GUI 509 can display a visual indication of the quality of the objects within the container 503 and/or a visual indication of the current mode of operation of the sensors 505. In some embodiments, the display 507 can include, but is not limited to, an e-paper display, a LED display, an OLED display, a LCD, or any other display suitable for presenting visual indications.

The computing system 511 and the display 507 may connect to the network 501 via a wired or wireless connection, in some embodiments. The computing system 511 may include one or more applications such as, but not limited to, a web browser, a sales transaction application, an object reader application, and the like. The computing system 511 may include some or all components described in relation to computing device 600 shown in FIG. 6.

In exemplary embodiments, the display 507 is in communication with the sensors 505 of the container 503 via a wired or wireless connection. The display 507, computing system 511, and database 515 may be in communication with each other via the communication network 501. The communication network 501 may include, but is not limited to, the Internet, an intranet, a LAN (Local Area Network), a WAN (Wide Area Network), a MAN (Metropolitan Area Network), a wireless network, an optical network, and the like. In one embodiment, the display 507 and computing system 511 can transmit instructions to each other over the communication network 501. In exemplary embodiments, the sensor thresholds 517 and sensor measurements 519 associated with objects in the container 503 can be stored at the database 515 and received at the display 507 or computing system 511 in response to a service performed by a database retrieval application.

Figure 6:
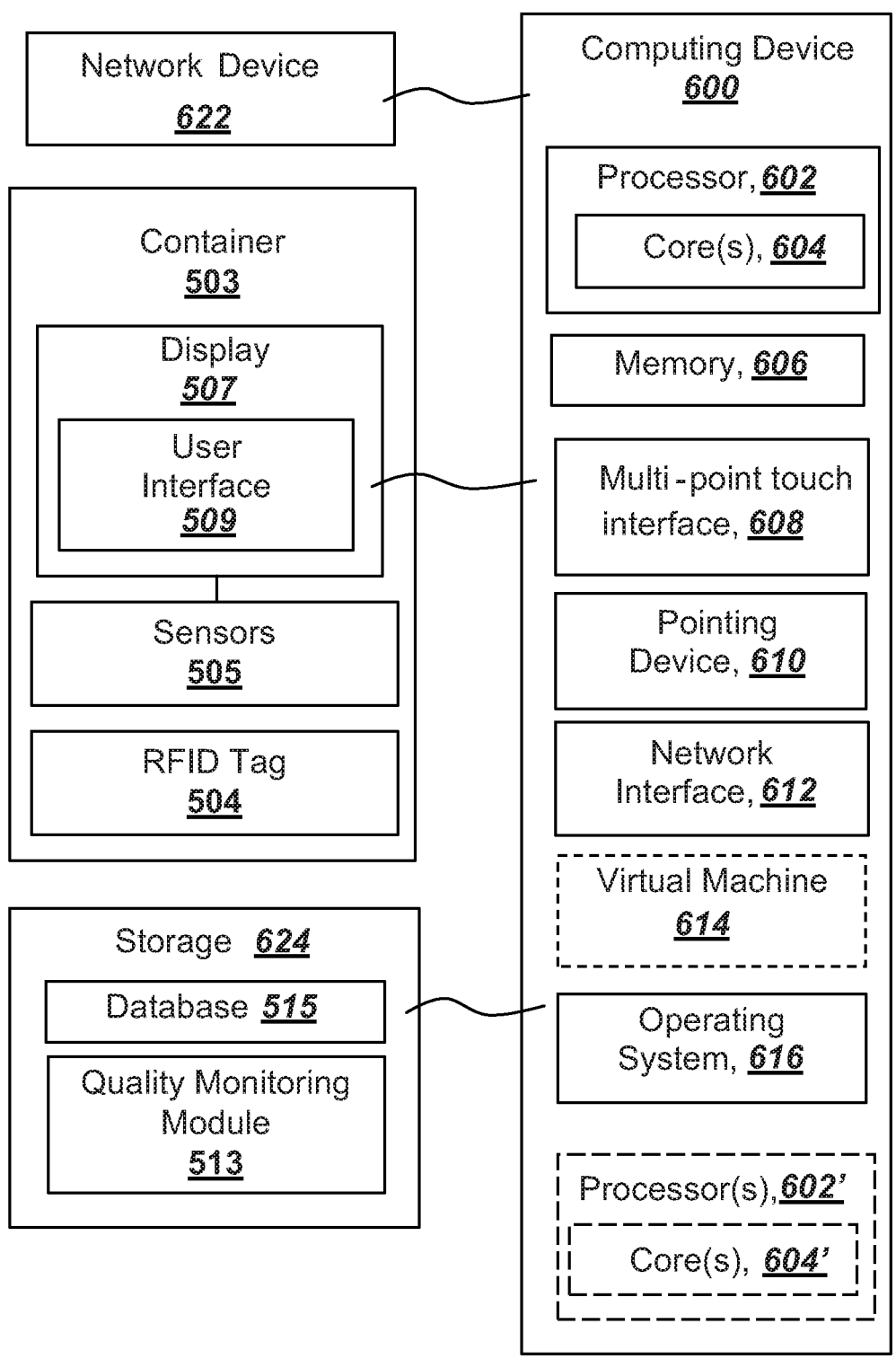
FIG. 6 is a block diagram of an exemplary computing device that can be used to perform exemplary processes in accordance with an exemplary embodiment.

FIG. 6 is a block diagram of an exemplary computing device 600 that can be used in the performance of any of the example methods according to the principles described herein. The computing device 600 includes one or more non-transitory computer-readable media for storing one or more computer-executable instructions (such as but not limited to software or firmware) for implementing any example method according to the principles described herein. The non-transitory computer-readable media can include, but are not limited to, one or more types of hardware memory, non-transitory tangible media (for example, one or more magnetic storage disks, one or more optical disks, one or more USB flashdrives), and the like.

For example, memory 606 included in the computing device 600 can store computer-readable and computer-executable instructions or software for implementing exemplary embodiments and programmed to perform processes described above in reference to FIGS. 1-4. The computing device 600 also includes processor 602 and associated core 604, and optionally, one or more additional processor(s) 602' and associated core(s) 604' (for example, in the case of computer systems having multiple processors/cores), for executing computer-readable and computer-executable instructions or software stored in the memory 606 and other programs for controlling system hardware. Processor 602 and processor(s) 602' can each be a single core processor or multiple core (604 and 604') processor.

Virtualization can be employed in the computing device 600 so that infrastructure and resources in the computing device can be shared dynamically. A virtual machine 614 can be provided to handle a process running on multiple processors so that the process appears to be using only one computing resource rather than multiple computing resources. Multiple virtual machines can also be used with one processor.

Memory 606 can be non-transitory computer-readable media including a computer system memory or random access memory, such as DRAM, SRAM, EDO RAM, and the like. Memory 606 can include other types of memory as well, or combinations thereof.

A user can interact with the computing device 600 through a display 507, such as an e-paper display, a LED display, an OLED display, a LCD, a touch screen display, or computer monitor, which can display one or more user interfaces 509 that can be provided in accordance with exemplary embodiments. The computing device 600 can also include other I/O devices for receiving input from a user, for example, a keyboard or any suitable multi-point touch interface 608, a pointing device 610 (e.g., a pen, stylus, mouse, or trackpad). The multi-point touch interface 608 and the pointing device 610 can be coupled to the display 507. The computing device 600 can include other suitable conventional I/O peripherals.

The computing device 600 can also include one or more storage devices 624, such as a hard-drive, CD-ROM, or other non-transitory computer readable media, for storing data and computer-readable instructions and/or software, such as quality monitoring module 513 that can implement exemplary embodiments of the methods and systems as taught herein, or portions thereof. Exemplary storage device 624 can also store one or more databases 515 for storing any suitable information required to implement exemplary embodiments. The databases 515 can be updated by a user or automatically at any suitable time to add, delete, or update one or more items in the databases. Exemplary storage device 624 can store one or more databases 515 for storing the sensor thresholds, sensors measurements, and any other data/information used to implement exemplary embodiments of the systems and methods described herein.

The computing device 600 can include a network interface 612 configured to interface via one or more network devices 622 with one or more networks, for example, Local Area Network (LAN), Wide Area Network (WAN) or the Internet through a variety of connections including, but not limited to, standard telephone lines, LAN or WAN links (for example, 802.11, T1, T3, 56 kb, X.25), broadband connections (for example, ISDN, Frame Relay, ATM), wireless connections, controller area network (CAN), or some combination of any or all of the above. The network interface 612 can include a built-in network adapter, network interface card, PCMCIA network card, card bus network adapter, wireless network adapter, USB network adapter, modem or any other device suitable for interfacing the computing device 600 to any type of network capable of communication and performing the operations described herein. Moreover, the computing device 600 can be any computer system, such as a workstation, desktop computer, server, laptop, handheld computer, tablet computer (e.g., the iPad® tablet computer), mobile computing or communication device (e.g., the iPhone® communication device), or other form of computing or telecommunications device that is capable of communication and that has sufficient processor power and memory capacity to perform the operations described herein.

The computing device 600 can run operating system 616, such as versions of the Microsoft® Windows® operating systems, different releases of the Unix and Linux operating systems, versions of the MacOS® for Macintosh computers, embedded operating systems, real-time operating systems, open source operating systems, proprietary operating systems, operating systems for mobile computing devices, or any other operating system capable of running on the computing device and performing the operations described herein. In exemplary embodiments, the operating system 616 can be run in native mode or emulated mode. In an exemplary embodiment, the operating system 616 can be run on one or more cloud machine instances.

In describing example embodiments, specific terminology is used for the sake of clarity. For purposes of description, each specific term is intended to at least include all technical and functional equivalents that operate in a similar manner to accomplish a similar purpose. Additionally, in some instances where a particular example embodiment includes system elements, device components or method steps, those elements, components or steps can be replaced with a single element, component or step. Likewise, a single element, component or step can be replaced with multiple elements, components or steps that serve the same purpose. Moreover, while example embodiments have been shown and described with references to particular embodiments thereof, those of ordinary skill in the art will understand that various substitutions and alterations in form and detail can be made therein without departing from the scope of the disclosure. Further still, other aspects, functions and advantages are also within the scope of the disclosure.

Example flowcharts are provided herein for illustrative purposes and are non-limiting examples of methods. One of ordinary skill in the art will recognize that example methods can include more or fewer steps than those illustrated in the example flowcharts, and that the steps in the example flowcharts can be performed in a different order than the order shown in the illustrative flowcharts.

What is claimed is:

1. A quality monitoring system comprising:
   a container configured to receive an object;
   a plurality of sensors configured to monitor a plurality of metrics associated with a quality of the object within the container;
   a display affixed to the container and configured to display a color-coded visual indication of the quality of the object within the container, the color-coded visual indication based at least in part on data collected from the plurality of sensors; and
   a quality monitoring module executed by a processor in a processing device, the quality monitoring module in communication with the plurality of sensors and the display and configured to control the plurality of sensors to switch operation between a first mode of operation and a second mode of operation based on a detected change in one of the plurality of metrics associated with a quality of an object being monitored by the plurality of sensors,
   wherein the second mode of operation changes one or more of a frequency of sampling or a type of operation of at least some of the plurality of sensors from the first mode of operation, and wherein the quality monitoring module instructs the plurality of sensors to transition from the first mode of operation to the second mode of operation based on a geographical location of the container.

2. The system of claim 1, wherein the plurality of metrics associated with a quality of the object within the container include at least two of temperature, pressure, off-gassing, weight and moisture.

3. The system of claim 1, wherein the quality monitoring module instructs the plurality of sensors to transition from the first mode of operation to the second mode of operation based on off-gas characteristics detected by the plurality of sensors.

4. The system of claim 1, wherein the quality monitoring module instructs the plurality of sensors to transition from the first mode of operation to the second mode of operation based on moisture characteristics detected by the plurality of sensors.

5. The system of claim 1, wherein the quality monitoring module is further configured to generate a notification in response to a metric associated with the quality of the object falling below a quality threshold value.

6. The system of claim 1, wherein the display is further configured to indicate a mode of operation of the sensors.

7. The system of claim 1, further comprising:
an RFID tag associated with the container that is configured to transmit data representative of the quality of the object or a mode of operation of the sensors.

8. The system of claim 1, further comprising:
a sensor configured to read a machine-readable code associated with the object.

9. A quality monitoring method comprising:
monitoring a plurality of metrics associated with a quality of an object within a container using a plurality of sensors;
displaying, via a display affixed to the container, a color-coded visual indication of the quality of the object within the container, the color-coded visual indication based at least in part on data collected from the plurality of sensors;
controlling the plurality of sensors to operate in a first mode of operation;
controlling the plurality of sensors to operate in a second mode of operation; and
instructing the plurality of sensors to switch between the first mode of operation and second mode of operation based on a detected change in one of the plurality of metrics associated with a quality of an object within the container,
transitioning from the first mode of operation to the second mode of operation based on a geographical location of the container,
wherein the second mode of operation changes one or more of a frequency of sampling or a type of operation of at least some of the plurality of sensors from the first mode of operation.

10. The method of claim 9, wherein the plurality of metrics associated with a quality of the object within the container include at least two of temperature, pressure, off-gassing, weight and moisture.

11. The method of claim 9, further comprising:
transitioning from the first mode of operation to the second mode of operation based on off-gas characteristics detected by the plurality of sensors.

12. The method of claim 9, further comprising:
transitioning from the first mode of operation to the second mode of operation based on moisture characteristics detected by the plurality of sensors.

13. The method of claim 9, further comprising:
generating a notification in response to a metric associated with the quality of the object falling below a quality threshold value.

14. The method of claim 9, wherein the display is further configured to indicate a mode of operation of the sensors.

15. The method of claim 9, further comprising:
transmitting, via an RFID tag associated with the container, data representative of the quality of the object or a mode of operation of the sensors.

16. The method of claim 9, further comprising:
reading a machine-readable code associated with the object using a sensor associated with the container.

17. A non-transitory machine readable medium storing instructions executable by a processing device, wherein execution of the instructions causes the processing device to implement a method for monitoring the quality of an object, the method comprising:
monitoring a plurality of metrics associated with a quality of an object within a container using a plurality of sensors;
displaying, via a display affixed to the container, a color-coded visual indication of the quality of the object within the container, the color-coded visual indication based at least in part on data collected from the plurality of sensors;
controlling the plurality of sensors to operate in a first mode of operation;
controlling the plurality of sensors to operate in a second mode of operation;
instructing the plurality of sensors to switch between the first mode of operation and second mode of operation based on a detected change in one of the plurality of metrics associated with a quality of an object within the container, and
transitioning from the first mode of operation to the second mode of operation based on a geographical location of the container,
wherein the second mode of operation changes one or more of a frequency of sampling or a type of operation of at least some of the plurality of sensors from the first mode of operation.

18. The medium of claim 17, wherein the plurality of metrics associated with a quality of the object within the container include at least two of temperature, pressure, off-gassing, weight and moisture.

19. The medium of claim 17, wherein execution of the instructions further causes the processing device to transition from the first mode of operation to the second mode of operation based on off-gas characteristics detected by the plurality of sensors.

20. The medium of claim 17, wherein execution of the instructions further causes the processing device to transition from the first mode of operation to the second mode of operation based on moisture characteristics detected by the plurality of sensors.

21. The medium of claim 17, wherein execution of the instructions further causes the processing device to generate a notification in response to a metric associated with the quality of the object falling below a quality threshold value.

22. The medium of claim 17, wherein the display is further configured to indicate a mode of operation of the sensors.

23. The medium of claim 17, wherein execution of the instructions further causes the processing device to transmit, via an RFID tag associated with the container, data representative of the quality of the object or a mode of operation of the sensors.

* * * * *